United States Patent
Pionteck et al.

(10) Patent No.: US 12,070,273 B2
(45) Date of Patent: Aug. 27, 2024

(54) SIMULATION OF THE DEPLOYMENT OF AN ENDOPROSTHESIS IN REAL TIME

(71) Applicants: THALES, Courbevoie (FR); ASSOCIATION POUR LA RECHERCHE ET LE DEVELOPPEMENT DE METHODES ET PROCESSUS INDUSTRIELS—ARMINES, Paris (FR); UNIVERSITE JEAN MONNET SAINT ETIENNE, Saint-Etienne (FR); CENTRE HOSPITALIER UNIVERSITAIRE SAINT-ETIENNE, Saint-Etienne (FR)

(72) Inventors: Aymeric Pionteck, Moirans (FR); Baptiste Pierrat, Aveizieux (FR); Sébastien Gorges, Moirans (FR); Jean-Noël Albertini, Sorbier (FR); Stéphane Avril, Saint-Etienne (FR)

(73) Assignees: THALES, Courbevoie (FR); ASSOCIATION POUR LA RECHERCHE ET LE DEVELOPPEMENT DE METHODES ET PROCESSUS INDUSTRIELS—ARMINES, Paris (FR); UNIVERSITE JEAN MONNET SAINT ETIENNE, Saint Etienne (FR); CENTRE HOSPITALIER UNIVERSITAIRE SAINT-ETIENNE, Saint Etienne (FR)

( * ) Notice: Subject to any disclaimer, the term of this patent is extended or adjusted under 35 U.S.C. 154(b) by 951 days.

(21) Appl. No.: 16/936,885

(22) Filed: Jul. 23, 2020

(65) Prior Publication Data
US 2021/0030474 A1 Feb. 4, 2021

(30) Foreign Application Priority Data

Jul. 29, 2019 (FR) ..................................... 1908569

(51) Int. Cl.
*G01N 33/48* (2006.01)
*A61B 34/10* (2016.01)
(Continued)

(52) U.S. Cl.
CPC .............. *A61B 34/10* (2016.02); *A61B 90/37* (2016.02); *A61B 90/39* (2016.02);
(Continued)

(58) Field of Classification Search
CPC ......... A61B 34/10; A61B 90/37; A61B 90/39; A61B 2034/102; A61B 2034/107;
(Continued)

(56) References Cited

U.S. PATENT DOCUMENTS

| | | |
|---|---|---|
| 2005/0010105 A1 | 1/2005 | Sra |
| 2008/0137923 A1 | 6/2008 | Spahn |
| 2013/0137974 A1* | 5/2013 | Sakaguchi ........... A61B 5/0044 378/98.2 |

FOREIGN PATENT DOCUMENTS

| | | |
|---|---|---|
| JP | 2013-135832 A | 7/2013 |
| JP | 2014-161674 A | 9/2014 |

(Continued)

OTHER PUBLICATIONS

Couprie, et al., "Discrete bisector function and Euclidean skeleton in 2D and 3D", Image and Vision Computing, vol. 25, Issue 10, Oct. 1, 2007.
(Continued)

*Primary Examiner* — Russell S Negin
(74) *Attorney, Agent, or Firm* — BakerHostetler (57) ABSTRACT

A device for medical imaging by X-ray is provided. More specifically, it relates to the simulation of the deployment of
(Continued)

an endoprosthesis in order to assist the surgeon in an endovascular surgical procedure. The invention makes use of a single 2D image in order to determine certain characteristics of a simplified model of the endoprosthesis: 2D positions, and deployment value of the stents; to determine the inherent rotation of at least one stent; then to determine the deployment of a model representing the structure of the stents, initialized on the basis of the preceding steps, in a 3D model of a vascular structure.

11 Claims, 10 Drawing Sheets

(51) Int. Cl.
  *A61B 90/00* (2016.01)
  *G01N 33/50* (2006.01)

(52) U.S. Cl.
  CPC ... *A61B 2034/102* (2016.02); *A61B 2034/107* (2016.02); *A61B 2090/367* (2016.02); *A61B 2090/376* (2016.02); *A61B 2090/3966* (2016.02)

(58) Field of Classification Search
  CPC ........ A61B 2090/367; A61B 2090/376; A61B 2090/3966
  See application file for complete search history.

(56) References Cited

FOREIGN PATENT DOCUMENTS

| JP | 2017-507685 A | 3/2017 |
| JP | 2017-86413 A | 5/2017 |
| JP | 2018-196717 A | 12/2018 |
| WO | 2011/121516 A2 | 10/2011 |
| WO | 2011/148299 A | 12/2011 |

OTHER PUBLICATIONS

Haigron, et al., "Angiovision: Aortic stent-graft placement by augmented angionavigation", IRBM, vol. 34, No. 2, pp. 167-175, Apr. 1, 2013.
Perrin, et al., "Patient-specific numerical simulation of stent-graft deployment: Validation on three-clinical cases", Journal of Biomechanics, vol. 48, No. 10, pp. 1868-1875, Jul. 1, 2015.
Auricchio, et al., "Patient-specific aortic endografting simulation: From diagnosis to prediction", Computers in Biology and Medicine, vol. 43, No. 4, pp. 386-394, Feb. 8, 2013.
Antiga, "Patient-specific modeling of geometry and blood flow in large arteries", Politecnico di Milano, Chapter 5: Geometric characterization of vascular structures, sections 5.2 to 5.5, 2002.
Duriez, "Real-time haptic simulation of medical procedures involving deformations and device-tissue interactions", (Doctoral dissertation, Université des Sciences et Technologie de Lille-Lille I), 2013.
English translation of Notice of Reasons for Rejection issued in Japanese Patent Application No. 2020-127068 dated Mar. 5, 2024.

* cited by examiner

SIMULATION OF THE DEPLOYMENT OF AN ENDOPROSTHESIS IN REAL TIME

CROSS-REFERENCE TO RELATED APPLICATIONS

This application claims priority to foreign French patent application No. FR 1908569, filed on Jul. 29, 2019, the disclosure of which is incorporated by reference in its entirety.

FIELD OF THE INVENTION

The present invention relates to the field of medical X-ray systems and more particularly to radiology systems used for endovascular surgery of aneurysms of the abdominal aorta.

BACKGROUND

Aneurysms of the abdominal aorta can be treated by conventional open surgery or by endovascular surgery. During an endovascular intervention, the surgeon does not have direct access to the operating site. On the contrary, in an endovascular operation, he makes an incision in the femoral artery at the groin region and inserts a very flexible metal wire. By pushing this wire, he can then move his tools, including the endoprosthesis, to the region of the aneurysm in the abdominal aorta. When he considers that the endoprosthesis is situated at the correct location, he can decide to release the endoprosthesis, which deploys automatically.

The correct positioning of the endoprosthesis is therefore crucial. Indeed, this prosthesis must be placed correctly and must not occlude arteries branching off from the main artery. In the most complex cases, so-called fenestrated endoprostheses comprise openings that have to be positioned precisely facing the ostia of the secondary arteries. For example, these openings have to be positioned facing the junctions between the aorta and the renal arteries, which issue from the latter. It is therefore essential to position the endoprosthesis correctly, in order to avoid obstructing these junctions and occluding the renal arteries.

In order to guide these manoeuvres, the surgeon uses a mobile interventional radiology system in order to precisely position the endoprosthesis, which will redirect the blood flow. These systems, also referred to as a mobile C-arm (or block amplifier), allow the surgeon to acquire X-ray images during the intervention and to monitor the position of the tools (catheter, prosthesis, etc.) in real time and in a minimally invasive manner. The majority of these systems make it possible to obtain two-dimensional images with a video image stream of up to thirty images per second. The practitioner then uses these images to mentally reconstruct the tool and the geometry of the artery, in order to validate its positioning in real time. This X-ray imaging requires injection of contrast agent. This contrast agent is indispensable for rendering the aorta visible to X-rays, but it has the disadvantage of being toxic. The possible number of injections and of image captures is thus limited.

The step of fitting an endoprosthesis in place is very complex in some cases and requires multiplying the image captures and consequently the irradiation of the patient and the volume of contrast agent injected. The probability of post-operative complications is also higher. In the short term, this is due to loss of blood and to the poor irrigation of the zones obstructed by the surgical tools. In the medium and long terms, imprecise positioning of the endoprosthesis leads to risks of leakage and thrombosis. The deployment of endoprostheses in the aorta takes place in 3D. A single 2D image may therefore prove inadequate for allowing the surgeon to clearly assess the deployment of the endoprostheses. The possibility of having access to a three-dimensional visualization of the operating site would therefore be a great advantage to the surgeon, allowing him to position his tools quickly and precisely, while reducing the number of angiographs.

There are currently several methods that permit this 3D visualization. However, these methods remain based on taking multiple 2D images from different viewing angles for the purpose of a 3D reconstruction. They therefore involve multiple injections of contrast agent, and the operating time is also increased because of the multiple images that have to be taken at different angles.

There is therefore a need for a tool that aids the surgical procedure, allowing the surgeon to visualize his tools and their configuration in the aorta of the patient, almost in real time and in 3D.

SUMMARY OF THE INVENTION

To this end, the invention relates to a method comprising: capture of a 2D image of a vascular structure by X-ray; acquisition of a 3D model of the vascular structure; acquisition of a model of an endoprosthesis in the vascular structure, comprising a plurality of stents; determination from the 2D image, and for each stent, of at least one position, at least one orientation, and at least one deployment value; simulation of the deployment in the 3D model of the vascular structure, for each stent, of a model of the stent representing the structure of the stent, said model of the stent being initialized on the basis of the model of the endoprosthesis; display of the deployed stent models.

Advantageously, the 2D image defines a 3D reference frame comprising a vertical axis and a horizontal axis and a depth axis of the image; in the endoprosthesis model, each stent is defined by: at least one position of at least one characteristic point and an orientation, which are defined by at least 6 degrees of freedom, including: the 3D position of a first characteristic point of the stent in the reference frame; an angle of intrinsic rotation; the at least one deployment value of the stent, defined about its central axis; the model of the stent is formed by a plurality of interconnected beam elements; said method comprising: determination from the 2D image, and for each stent, of at least one position, at least one orientation, and at least one deployment value; of the at least one characteristic point along the vertical axis and horizontal axis and the at least one deployment value of said stent; determination, for at least one stent, of its angle of intrinsic rotation.

Advantageously, the position and the orientation of each stent are defined by the 3D positions of three characteristic points corresponding respectively to the centre, the upper end and the lower end of the stent along its central axis, and the intrinsic rotation of the stent about its central axis.

Advantageously, the determination, for at least one stent, of its angle of intrinsic rotation comprises the determination of the angle of intrinsic rotation for which at least one 3D position projection of at least one radiopaque marker on the stent most closely matches to at least one image of the at least one marker on the 2D image.

Advantageously, the angle of intrinsic rotation is obtained by the execution of a loop minimizing the distance between the at least one projection and the at least one image of the at least one marker on the 2D image, as a function of the angle of intrinsic rotation.

Advantageously, the determination, for at least one stent, of its angle of intrinsic rotation comprises modelling the stent in the form of a beam element of a finite element model, between a characteristic point representing the upper end of the central axis of the stent and a characteristic point representing the lower end of the central axis of the stent, in which the characteristic points are free of displacements along the depth axis.

Advantageously, the endoprosthesis is represented in the form of a finite element model in which: each stent is modelled by a beam element, the successive stents being connected to each other by at least one beam element; the positions of the characteristic points of the stents whose maximum diameter of deployment is greater than or equal to the diameter of the vascular structure at the deployment position are fixed along the vertical axis, horizontal axis and depth axis; the positions of the characteristic points of the stents whose maximum diameter of deployment is less than the diameter of the vascular structure at the deployment position are fixed along the vertical axis and horizontal axis and are free in displacement along the depth axis; the positions of the characteristic points of the stents whose maximum diameter of deployment is less than the diameter of the vascular structure at the deployment position along the depth axis are determined by the mechanical equilibrium of the finite element model.

Advantageously, the display of the deployed stent models comprises the display in superposition of the projection of the stent models on the 2D image of the vascular structure.

Advantageously, the display of the deployed stent models comprises the 3D display of the deployed stent models and of the 3D model of the vascular structure.

Advantageously, the 3D model of the vascular structure is a finite element model representing the central line of the vascular structure by beam elements.

The invention also describes a computer program product comprising computer code elements configured for executing a method according to one of the embodiments of the invention.

The invention also describes a device comprising: at least one input port configured to receive a 2D image of the vascular structure captured by X-ray; at least one calculation unit configured to execute a method according to one of the embodiments of the invention.

The method as a whole permits a both reliable and rapid calculation of the deployment of an endoprosthesis in the aorta. For example, the method can be carried out in about thirty seconds on standard calculation means, which allows the deployment of the endoprosthesis to be modelled almost in real time.

The method of the invention provides the surgeon with real-time visualization of the deployment of the endoprosthesis on the basis of its actual position. This therefore makes it possible to considerably improve the precision of the treatment performed by the surgeon.

The method of the invention requires a single image capture in order to simulate the deployment of an endoprosthesis, which avoids the use of multiple injections of contrast agent.

The method is applicable to prostheses that are deployed and also to prostheses that are not deployed or that are partially deployed.

BRIEF DESCRIPTION OF THE DRAWINGS

Other features, details and advantages of the invention will become clear from reading the description provided with reference to the attached drawings which are given as examples and in which.

DETAILED DESCRIPTION

Figure 1:
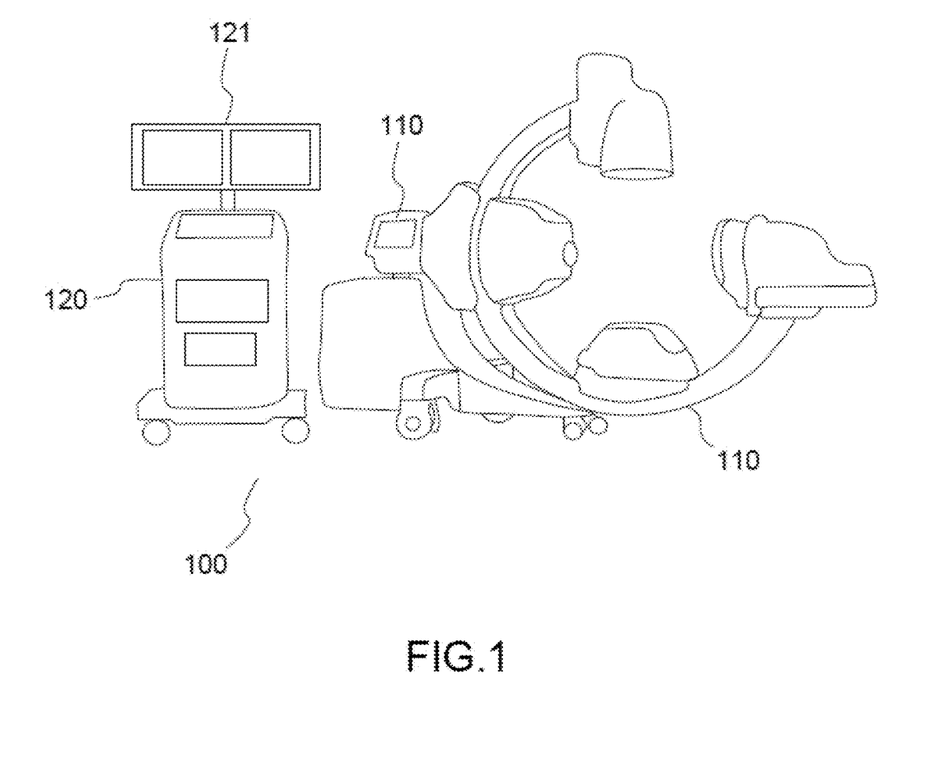
FIG. 1 shows a medical imaging system in which the invention can be implemented.

FIG. 1 shows a medical imaging system in which the invention can be implemented.

The system 100 is a mobile interventional radiology system.

It comprises an element called a C-arm 110, allowing X-ray images to be taken of the body of a patient. The C-arm is able to turn about different axes in order to capture images of a stationary patient at different angles. The C-arm comprises a control interface allowing the medical team to control the orientation and the image capture.

The C-arm 110 is connected to a calculation device, for example a computer 120, able to generate the display of the X-ray image, taken by the C-arm 110, on display means, for example screens 121. For this purpose, the calculation device 120 comprises an inlet port for receiving the perioperative images. The calculation device 120 also comprises at least one calculation unit (for example a processor) for processing the images taken by the C-arm. For example, the processor can perform a pre-analysis of the image and can superpose, on the image, items of information that may be of interest to the medical team (for example the time when the image was captured, the temperature of the patient, his or her blood pressure, etc.).

The separation of the system into two devices, respectively the C-arm 110 for taking the images, and the calculation device 120 for processing and displaying them, permits great flexibility in the use of the C-arm 110, which can remain mobile even if the position of the display screens 121 remains fixed.

In a set of embodiments of the invention, this device 120 also makes it possible to generate a visualization of the deployment of an endoprosthesis and to generate its display in 2D or 3D, as will be explained below.

The system 100 is given solely as an example of a system in which the invention could be implemented. The invention could be implemented in numerous other medical systems. For example, according to different image capture modes, the processing and the display of the images can be performed in a single device. It is also possible to capture an image at one location and send the image for processing and display thereof to another site, for example on a remote server.

Figure 2A:
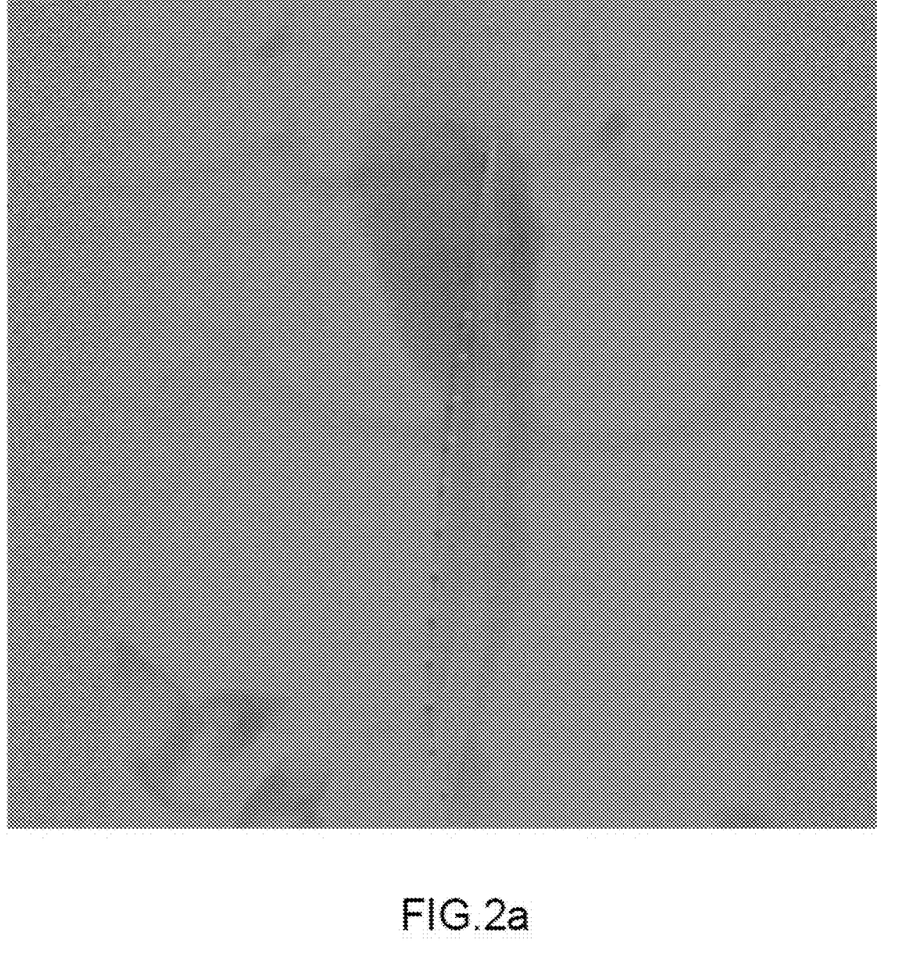
FIG. 2a shows a perioperative 2D image showing an endoprosthesis in the aorta, with injection of contrast agent.
Figure 2B:
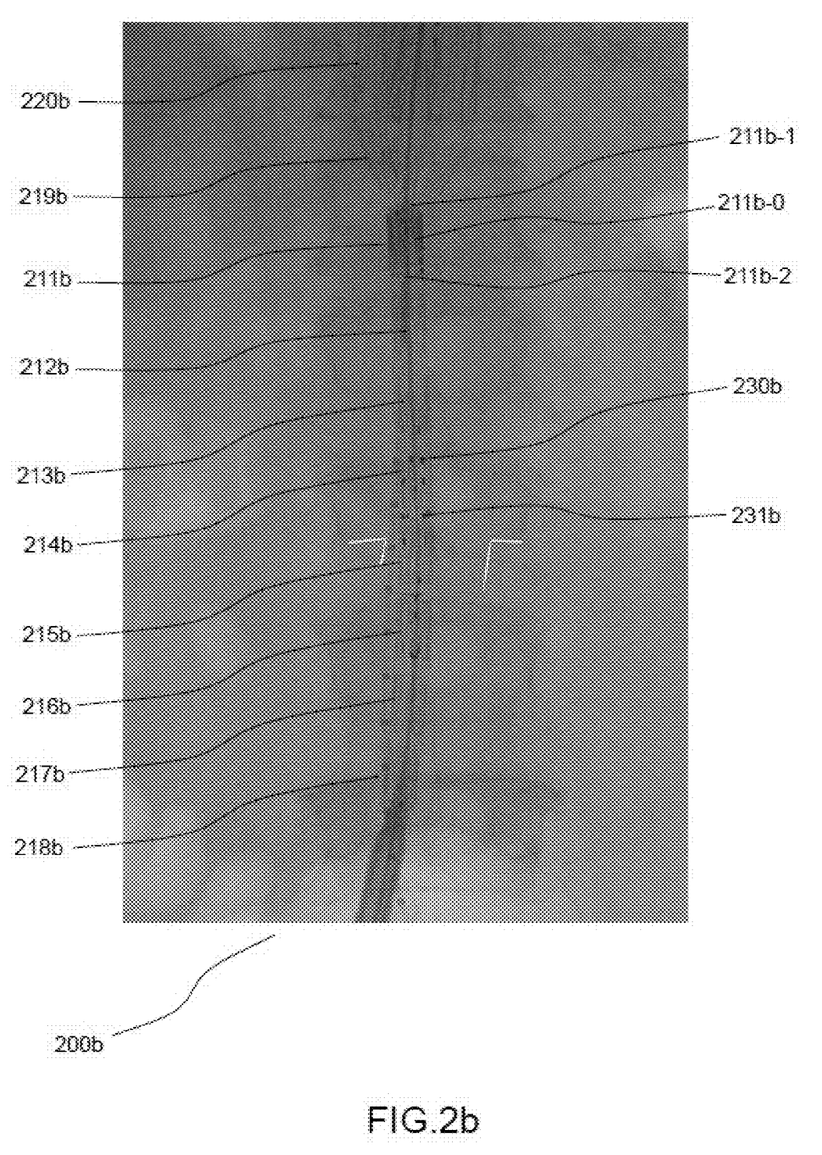
FIG. 2b shows a perioperative 2D image showing an endoprosthesis in the aorta, without injection of contrast agent.
Figure 2C:
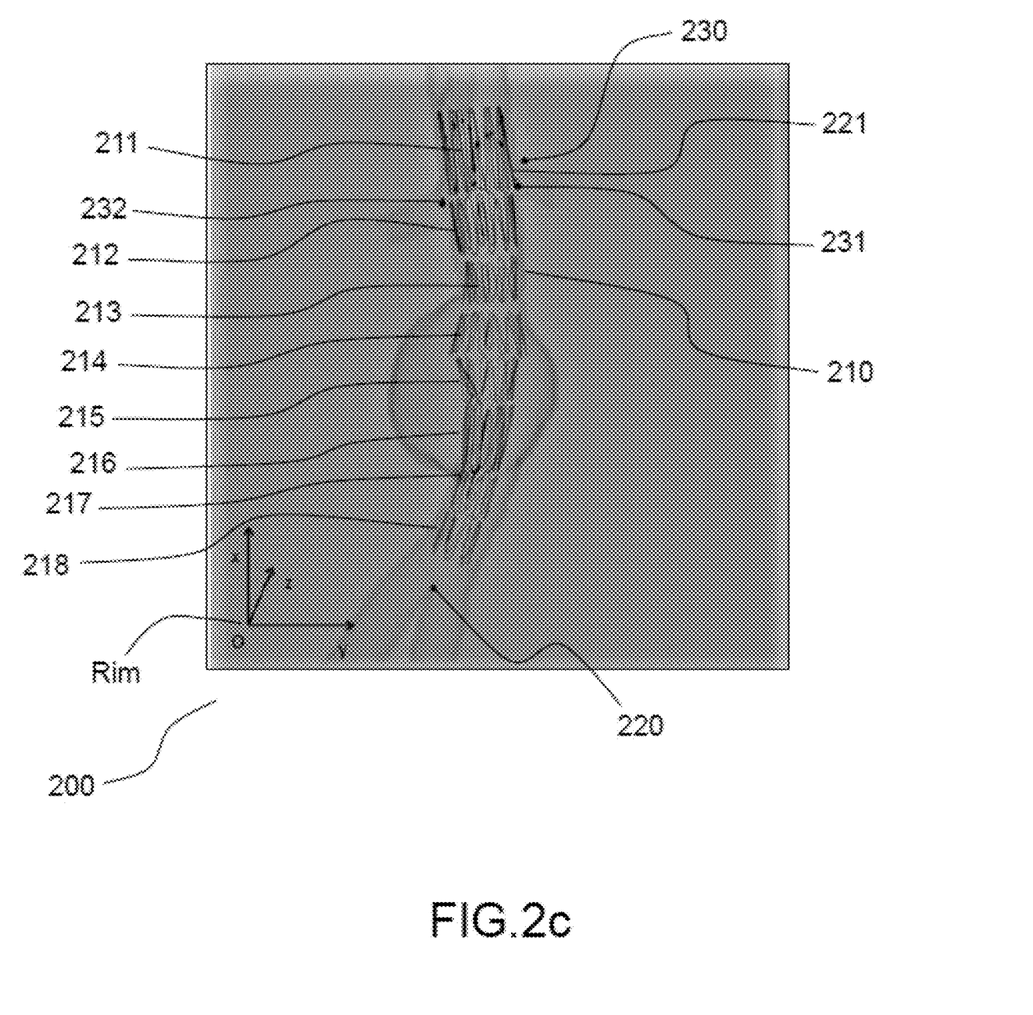
FIG. 2c shows an endoprosthesis deployed in a mock-up aorta, according to a set of implementations of the invention.

FIGS. 2a, 2b and 2c show respectively a perioperative 2D image showing an endoprosthesis in the aorta, with and without injection of contrast agent, and an endoprosthesis deployed in a mock-up aorta according to a set of implementations of the invention.

FIG. 2a shows a perioperative image of the aorta taken by X-ray, for example by a device such as the device 100, and taken with contrast agent. This image permits visualization of the boundaries of the aorta. In particular, it makes it possible to know the diameter of the aorta at each point and to visualize from where the adjacent veins branch off.

FIG. 2b shows a perioperative image 200b of the aorta taken by X-ray, for example by a device such as the device 100, taken without contrast agent and before deployment of the stents. Without contrast agent, the boundaries of the aorta are no longer discernible, but the stents 211b, 212b, 213b, 214b, 215b, 216b, 217b and 218b, 219b, 220b of the endoprosthesis are apparent. The stents 211b to 218b are not deployed, the stent 219b is partially deployed, and the stent 220b is completely deployed. The radiopaque markers, such as the markers 230b and 231b, are also apparent. Perioperative imaging also makes it possible to locate certain critical characteristic points which may, for example, be visualized by a marker such as the markers 230b and 231b. These markers can be positioned at particularly important points on the endoprosthesis in order to allow the surgeon to locate them on the perioperative image.

When introducing the endoprosthesis, the surgeon can capture a first image with injection of contrast agent in order to visualize the boundaries of the aorta, then one or more images without contrast agent, in order to visualize the position of the stents and the radiopaque markers. These two views can be displayed in superposition in order to visualize the position of the stents within the aorta.

At this stage, the endoprosthesis may be non-deployed, partially deployed or fully deployed. However, an image such as the one in FIG. 2b allows the positions of the stents to be determined, as will be explained below.

The perioperative 2D images of this type thus allow the surgeon to have a general view of the position and deployment of endoprostheses in an artery. However, a 2D view of this kind may often prove inadequate for assessing a deployment which, by its very nature, takes place in 3D.

FIG. 2c shows an image of an endoprosthesis deployed in a mock-up. This image is similar to what a surgeon sees by superposition of a perioperative image with contrast agent and of a perioperative image without contrast agent, that is to say visualizing both the endoprosthesis and the space in which the latter deploys. In the example of FIG. 2c, the endoprosthesis is completely deployed. This image shows an endoprosthesis deployed in a mock-up of the aorta 220. The endoprosthesis is formed by a plurality of stents 211, 212, 213, 214, 215, 216, 217, 218. The perioperative image thus permits visualization, in 2D, of the position and deployment of the stents within an artery.

As will be explained below, the invention makes it possible, on the basis of a 2D image, to obtain a 3D simulation and visualization of the deployment of an endoprosthesis. In the remainder of the description, the 3D deployment will be expressed according to a reference frame $R_{im}$, based on three axes x, y and z, which correspond respectively to a vertical axis, a horizontal axis and a depth axis. The plane formed by the vertical axis x and horizontal axis y is called the plane of projection or the plane of the 2D image. However, this reference frame is given solely by way of example, and it will be possible for a person skilled in the art, on reading the present disclosure, to choose any 3D reference frame meeting his needs.

Figure 3:
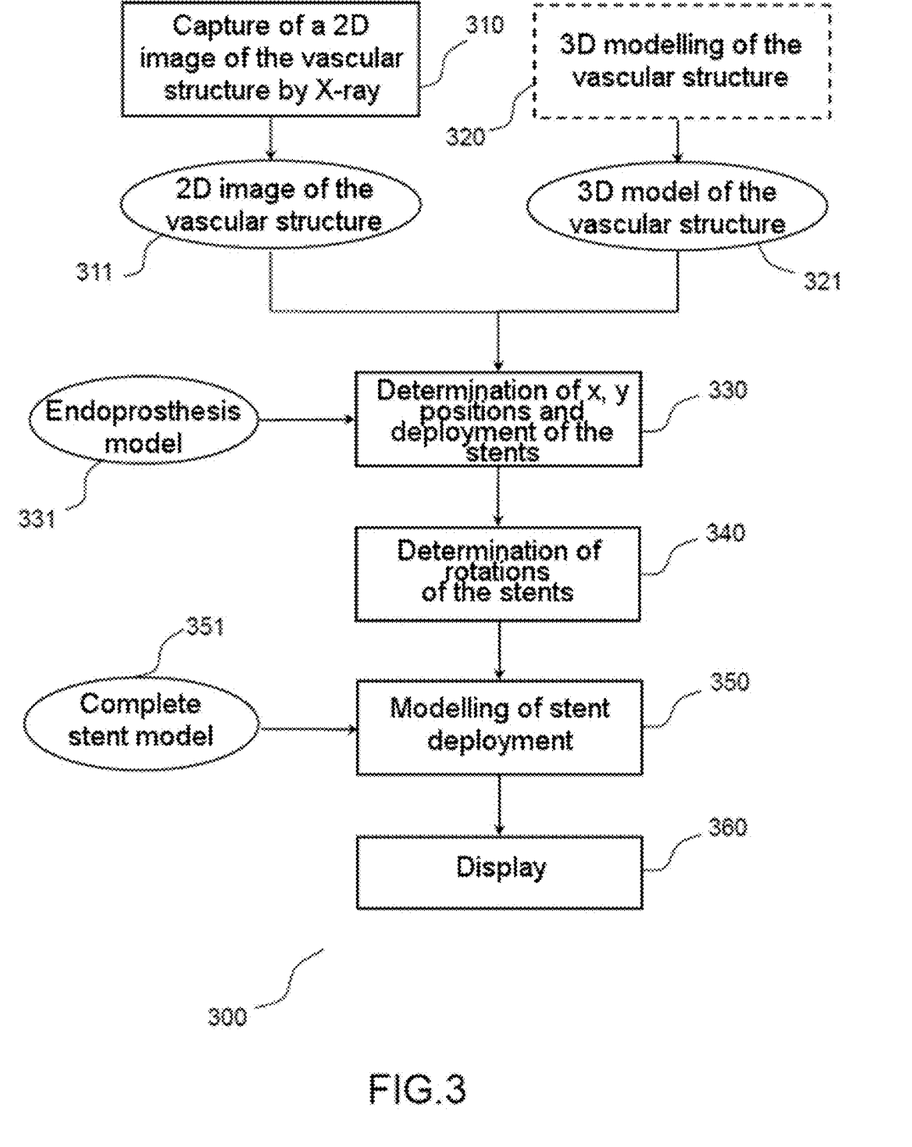
FIG. 3 shows a method of simulating the deployment of an endoprosthesis, according to a set of implementations of the invention.

FIG. 3 shows a method of simulating the deployment of an endoprosthesis according to a set of implementations of the invention.

The aim of the method 300 is to simulate the deployment of an endoprosthesis and to allow a surgeon to visualize the deployment of an endoprosthesis in an artery, if appropriate in 3D.

The method 300 comprises a step 310 of capturing a 2D image 311 of a vascular structure by X-ray. This 2D image is a perioperative image and can be taken, for example, by a device of the C-arm type, such as the device 100. The images in FIGS. 2a and 2b are two examples of such an image. As has been explained above, the capture of such an image by X-ray can comprise an injection of contrast agent into the vascular structure. It should be noted that, in the remainder of the description, the method will be illustrated by examples relating to the simulation of an endoprosthesis in the aorta. However, these examples are given as non-limiting examples, and the method may be applied to the simulation of endoprosthesis deployment in any vascular structure. There is no fundamental difference between the deployment of an endoprosthesis in the aorta and in another vascular structure, and therefore the method may be applied directly to other vascular structures. The method is also applicable to the simulation of deployment of the endoprosthesis in surgical mock-ups.

The capture of the 2D image defines a 3D reference frame which will be used in the rest of the method. This 3D reference frame comprises a vertical axis, a horizontal axis and a depth axis of the image capture. In the example in FIG. 2, these axes are labelled x, y and z, respectively. However, this nomenclature is given solely by way of example, and it will be a simple matter for a person skilled in the art to provide the axes with the names and orientations that meet his needs.

The method 300 also comprises the acquisition of a 3D model 321 of the aorta. This 3D model 321 makes it possible to define the contours and the volume of the aorta in 3D. The aorta can be defined, for example, by a set of 3D polygons. The boundaries of the aorta can thus be expressed in the reference frame defined by the 2D imaging.

According to different embodiments of the invention, the 3D model can be obtained in different ways. For example, it may have been created beforehand for the patient by 3D imaging, obtained beforehand and then registered in real time during the operation, or it may be created from the perioperative 2D images.

In a set of embodiments of the invention, the 3D model of the aorta 321 is a finite element model, comprising a representation of the central line of the aorta and of the surface thereof.

In a set of implementations of the invention, the 3D model of the aorta is obtained from a perioperative 2D image, for example an image obtained from a C-arm, by a method of non-rigid registration of a previous model of the aorta.

As has been indicated above, the method of non-rigid registration of the aorta is based on a finite element model of the central line of the artery. The perioperative information items contained in the plane of projection of the perioperative 2D image serve as boundary conditions on the finite element model. The deformations outside the plane are then calculated by the mechanical model.

In a set of embodiments of the invention, the registration method has the following steps:

- the central line of the artery is extracted using the Voronoi diagram method, introduced for example by Antiga, L. (2002). Patient-specific modeling of geometry and blood flow in large arteries. Politecnico di Milano;
- the central line is implemented in a finite element model based on beam elements. This can be done in different ways. Duriez, C. (2013). Real-time haptic simulation of medical procedures involving deformations and device-tissue interactions (Doctoral dissertation, Université des Sciences et Technologie de Lille-Lille I) provides an example of implementation of the central line of the aorta via a finite element model;
- a first 2D/2D non-rigid registration is performed between the perioperative images and the projection of the central line extracted in the preceding step. This non-rigid registration is composed of a rigid registration then an interpolation;
- the 2D information items concerning the position of the aorta or of the tools during surgery are then implemented in the finite element model. The matrix of projection of the perioperative images is assumed to be known. By this means, it is possible to calculate the back-projection lines of each of the characteristic points identified on the 2D images. These information items are then implemented in the mechanical model in the form of boundary conditions, the points of the 3D model being forced to move along the back-projection lines. Thus, the mechanical model calculates the deformations that are not contained in the plane of projection of the perioperative 2D image in order to reach a state of equilibrium;
- the volume of the aorta is then recreated around the updated central line.

In a set of embodiments of the invention, the 3D model of the aorta is superposed on the perioperative images.

The method 300 also comprises the acquisition of a model 331 of the endoprosthesis. In this model, each stent is defined by at least one position and one orientation of the stent, which are defined by at least 6 degrees of freedom, and a deployment of the stent.

The degrees of freedom representative of the position and orientation of the stent comprise at least one 3D position of at least one characteristic point of the stent, and an intrinsic rotation $r_{x'}$ of the stent about its central axis. According to different embodiments, the 6D position of the stent can be defined in different ways. For example, it can be defined by the 3D position of at least two characteristic points of the stent and an angle of intrinsic rotation, or by the 3D position of a single characteristic point of the stent and three angles of rotation. A person skilled in the art will be easily able to define the type of stent modelling that meets his needs.

Figure 4:
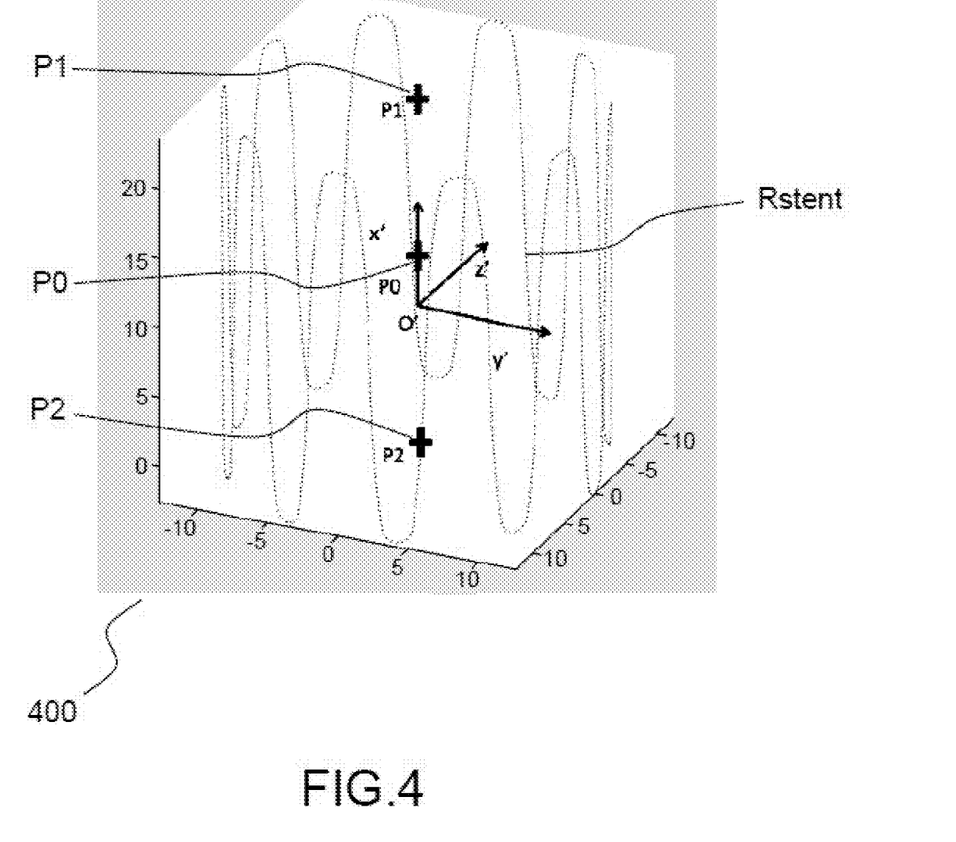
FIG. 4 shows a modelling of a stent within an endoprosthesis model, according to a set of implementations of the invention.

FIG. 4 shows a modelling of a stent within an endoprosthesis model according to a set of implementations of the invention.

FIG. 4 shows the modelling 400 of a stent within an endoprosthesis model 331.

In this example, the stent is associated with its own reference frame $R_{stent}$ comprising 3 axes (x', y', z') initially aligned with the axes (x, y, z) of the reference frame $R_{im}$. The intrinsic rotation of the stent $r_{x'}$ is defined about the central axis (which can also be called the vertical axis) x'. This simplified model comprises the 3D position of three characteristic points P0, P1, P2, corresponding respectively to the centre, the upper end and the lower end of the stent along its central axis x'. In this example, the position and the orientation of the stent are thus defined by 10 degrees of freedom (9 degrees for the three 3D positions, and one degree for the rotation).

This use of three characteristic points makes it possible to further improve the determination of the position and the orientation of the stent.

However, this modelling of the position and orientation of a stent is given solely as a non-limiting example, and the position and orientation of a stent could be represented in other ways. For example, they could be represented by the position of the characteristic point P0 and 3 rotations, or the positions of the characteristic points P1 and P2 and the intrinsic rotation about the axis x'.

Figure 5:
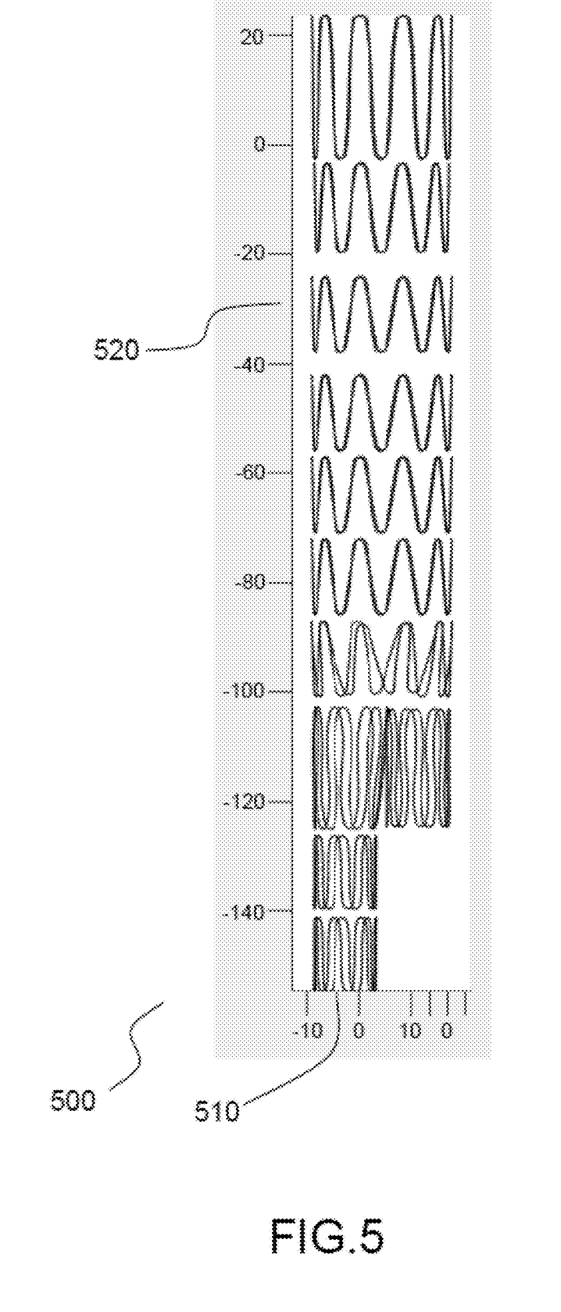
FIG. 5 shows the deployment of a stent within the context of a model of the endoprosthesis.

FIG. 5 shows the deployment of a stent in the context of a model of the endoprosthesis.

In a set of embodiments of the invention, the deployment of the stent is defined by a single value. This value can be, for example, the diameter of the stent, a percentage or a ratio of deployment.

The diagram 500 shows the simplified deployment of several stents. The axis 510 shows the deployment of the stent in mm. The axis 520 shows the position and the length of each stent.

It is also possible, according to different embodiments of the invention, to represent the deployment of the stent according to a limited number of values representing the deployment of the stent at different characteristic points about its central axis. For example, the deployment of the stent can be represented by a deployment value at the upper end of the stent and a deployment value at its lower end.

The representation of the deployment of the stent by at least one value representative of a level of deployment of the stent about its central axis thus makes it possible, in combination with the position and orientation values, to represent the deployment of each stent within the endoprosthesis in a highly synthetic manner, with the aid of a limited number of parameters, of which most of the values can be extracted from a 2D perioperative image.

The model 331 of the endoprosthesis thus permits a simplified modelling of the endoprosthesis, making it possible to represent the overall positioning of the endoprosthesis with a limited number of degrees of freedom.

Returning to FIG. 3, the method 300 comprises a step 330 of determining from the 2D image, and for each stent, the at least one position of the at least one characteristic point along the vertical axis (x) and horizontal axis (y) and the at least one deployment value of said stent.

This step involves identifying all the values of the endoprosthesis model that can be obtained directly from the 2D image.

Figure 6:
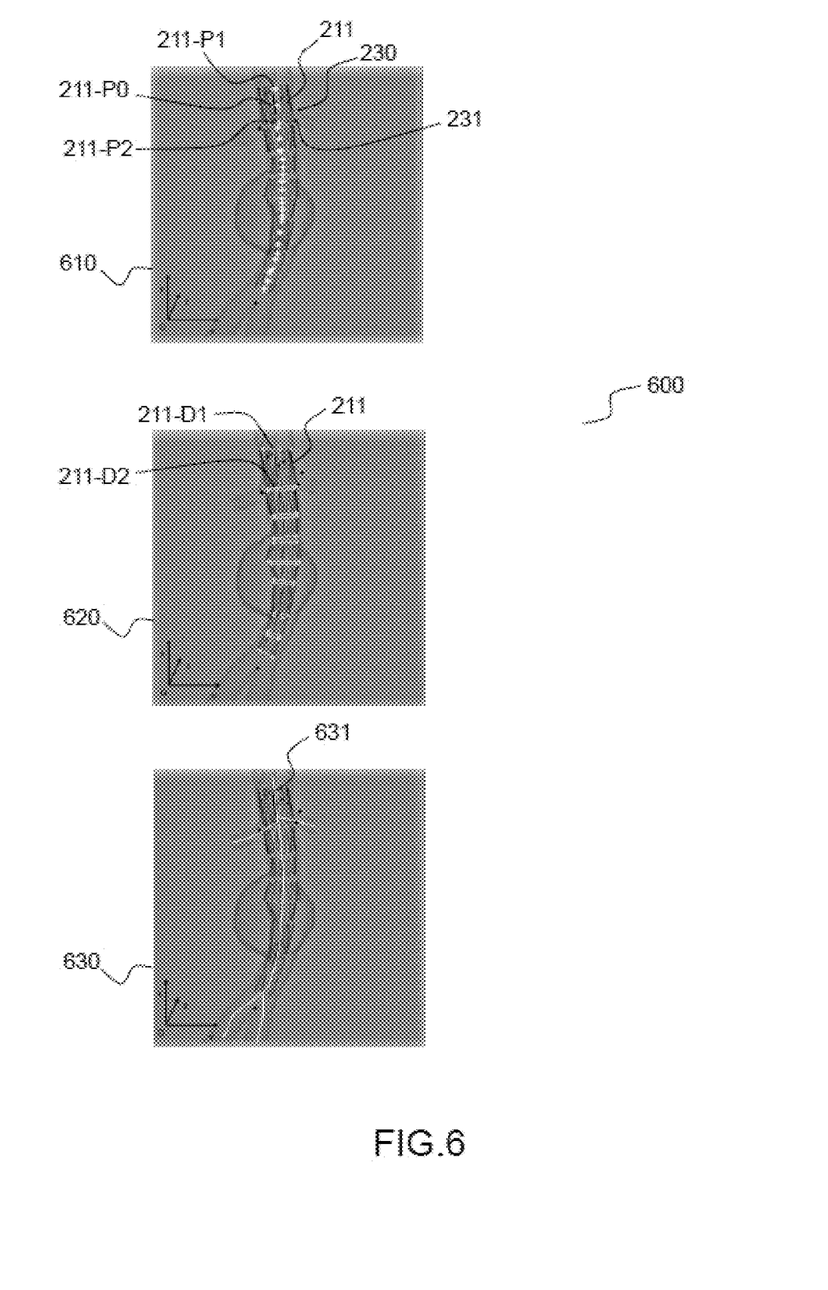
FIG. 6 shows the determination, on the basis of the 2D image, of the vertical and horizontal positions of the characteristic points of the stents, and also the deployment thereof.

FIG. 6 shows the determination, from the 2D image, of the vertical and horizontal positions of the characteristic points of the stents, and of the deployment of said stents.

More precisely, FIG. 6 shows the image of FIG. 2c, on which different parameters for modelling the deployment of the endoprosthesis in 3D are highlighted. FIG. 6 thus shows the detection of certain values on the perioperative image of the aorta, on a 2D image similar to the ones that a surgeon could visualize in real time. Although FIG. 2c and FIG. 6 show an endoprosthesis deployed in a mock-up of the aorta, the elements presented in FIG. 6 are also applicable to an image showing the aorta, highlighted by virtue of the contrast agent, in superposition with an image of the endoprosthesis, and also to images of the endoprosthesis when not deployed or when partially deployed.

The three vignettes 610, 620 and 630 respectively show three examples of determination, on the image 200, of the positions of the characteristic points of the stents, the deployment of the stents, and the association with the central line of the aorta.

In particular, the 2D image makes it possible to obtain directly, as shown in FIG. 2b, the positions of each of the characteristic points of the stents along the x and y axes of the reference frame $R_{im}$. The reading can be done manually from the information items shown on the screen, or semi-automatically from processing in which the position of the centres of gravity of the stents is detected. In the example shown in FIG. 6, the stent 211 is associated with three characteristic points 211-P1, 211-P0 and 211-P2, according to the model shown in FIG. 4. The analysis of the image 200b thus makes it possible to deduce directly the positions of the characteristic points 211-P0, 211-P1 and 211-P2 along the x and y axes, for each stent. For example, these points can correspond to the points 211b-0, 211b-1 and 211b-2 of the image 200b, the position of which can be determined directly by analysis of the image 200b. According to different embodiments of the invention, the positions x, y of the characteristic points can be determined with respect to a single origin of the reference frame $R_{im}$, or with respect to a central point of the aorta. The stents are then positioned in the simulation by virtue of the positions of the characteristic points that are thus determined.

The vignette 620 shows the determination, for each stent, of at least one deployment value of said stent about its central axis. In the example of FIG. 6, each stent is associated with a deployment value of its upper end and a deployment value of its lower end. For example, the stent 211 is associated with a deployment value 211-D1 at its upper end and with a deployment value 211-D2 at its lower end. Here once again, the deployment values of the stent can be obtained directly by analysis of the image 200. In the example of the vignette 620, the stents are deployed, and the deployment value can be obtained directly by measuring the deployment of the stents on the image, manually or automatically by image analysis.

In embodiments in which the endoprosthesis is not deployed or not fully deployed, the deployment value can be determined as the diameter of the aorta at the point of deployment, if the maximum diameter of deployment of the endoprosthesis is greater than or equal to said diameter of the aorta at the point of deployment. In the opposite case, the deployment value corresponds to the maximum deployment of the endoprosthesis. Indeed, the final deployment diameter of the endoprosthesis at this point will in this case be constrained either by the diameter of the aorta or by the diameter of the stent.

The vignette 630 shows the association between the characteristic points of the stents and the central line of the aorta.

The central line of the aorta can be obtained by projection of a previously obtained 3D central line, or by a method of skeletonization of the 2D image (numerous methods of skeletonization of the 2D image are known, for example the method described by Couprie, M., Coeurjolly, D., & Zrour, R. (2007). Discrete bisector function and Euclidean skeleton in 2D and 3D. *Image and Vision Computing*, 25(10), 1543-1556). In a set of embodiments of the invention, the position of the characteristic points of the stent along the z axis is initialized on the central line of the aorta.

As is shown in FIG. 6, the step 330 of determination of the horizontal and vertical positions and of the deployments of the stents can be done by direct analysis of a perioperative 2D image, either manually or automatically by image analysis.

This determination is thus carried out very quickly. The step 330 can thus be effected in real time once the 2D image has been captured. Moreover, this step permits great precision, to less than a millimetre, on the values determined.

Certain characteristics of the model of the endoprosthesis cannot be determined directly by the direct analysis of the image. For example, the position of the characteristic points on the depth axis z and the intrinsic rotation of the stents cannot be determined directly. These values can be initialized to default values. For example, the positions of the points on the depth axis can be initialized such that the points are situated on the central line of the aorta, and the intrinsic rotation of the stent about the axis x' can be initialized to 0.

In a set of embodiments of the invention, the endoprosthesis assembly is modelled in the form of a finite element model in which each stent is modelled by a beam element, and the stents are connected to each other by small beam elements.

In a set of embodiments of the invention, a plurality of connecting beam elements (for example five) are arranged in series between the ends of the beam elements representing the stents. These connecting beam elements can be associated with stiffness matrices, of which the mechanical characteristics are different from those of the stiffness matrices of the beam elements representing the stents. Thus, these connecting beam elements will have a less rigid behaviour. This makes it possible to precisely model the mechanical equilibrium between the successive stents.

The stents whose maximum diameter of deployment is greater than or equal to the diameter of the aorta, at the site of deployment, are considered as constrained: the position of their characteristic points is fixed along the axes x, y and z. Indeed, their position will be completely constrained by the volume of the aorta at the time of their deployment. By contrast, those whose maximum diameter of deployment is smaller than the diameter of the aorta are considered "free": their characteristic points are constrained in displacement along the horizontal axis z and vertical axis y but free in displacement along the z axis. Their position along the depth axis z is then defined by the mechanical equilibrium of the finite element model.

This makes it possible to obtain a precise 3D position of the stents whose position is not completely constrained by the volume of the aorta, while taking into account the equilibrium of the mechanical forces within the aorta.

The positioning of the characteristic points of the stents on the central line of the aorta provides a good compromise between the calculation time and the precision of the method.

Returning to FIG. 3, the method 300 comprises a step 340 of determination of the intrinsic rotation angle of at least one stent of the endoprosthesis.

According to different embodiments of the invention, this step, performed on each stent separately, can be performed on all or some of the stents of the endoprosthesis. For example, it can be performed on each stent of the endoprosthesis. It can also be performed on certain critical stents only, for example stents comprising a window that is to be positioned facing an ostium. The surgeon can also manually select the stents on which to perform this step according to his needs.

In a set of embodiments of the invention, the determination, for at least one stent, of its angle of intrinsic rotation $r_x'$ comprises the determination of the angle of intrinsic rotation $r_x'$ for which the projection of the position of at least one radiopaque marker most closely matches to the image of this marker on the 2D image. For example, in the image 200 also represented in vignettes 610, 620 and 630 in FIG. 6, the stent 211 comprises a certain number of radiopaque markers, such as the markers 230 and 231. The position of these radiopaque markers is known in the simplified model of the stent. Thus, knowing the deployment values of the stent, it is possible, for each value of the angle of intrinsic rotation $r_x'$, to project the 3D position of the radiopaque marker onto the 2D image and to check whether it tallies with the position of the radiopaque marker on the 2D imaging. This comparison can be carried out for one or several markers.

The determination of $r_x'$ can thus be effected in different ways. For example, the angle of intrinsic rotation $r_x'$ can be obtained by executing a loop minimizing the distance between the projections of the 3D positions and the images of the at least one marker on the 2D image, as a function of the angle of intrinsic rotation $r_x'$.

Thus, the angle $r_x'$ can be modified iteratively, and at each iteration the position difference, for each marker, between the projection of its 3D position in the model on the 2D image and its image taken by X-ray can be calculated. If several markers are used, the absolute values of the position differences can be added together or taken separately. Thus, the values of the angles $r_x'$ can be determined iteratively in order to minimize the position differences between the projections of the 3D positions and the images of the one or more markers on the 2D imaging, for example by way of a gradient descent algorithm in stochastic methods, or any other algorithm by which it is possible to identify a global minimum of the differences between the projections of the 3D positions of the markers and their images, as a function of the intrinsic rotation $r_x'$. According to different embodiments of the invention, such algorithms can be initialized with a single point of departure, or with multiple points of departure in order to avoid convergence towards a local minimum. Any minimization algorithm can be used here.

This provides a simple and quick way of determining the intrinsic rotation $r_x'$ of a stent.

The method 300 then comprises the simulation of the deployment in the 3D model of the aorta 311, for each stent, of a model of the stent 351 formed by a plurality of beam elements and initialized on the basis of the model 331 of the endoprosthesis 210.

Once the values of the parameters of the model 331 of the endoprosthesis have been determined, in which each stent is represented in a simplified manner, this step involves using these parameter values to initialize a more complex model of each stent and to simulate its deployment in the 3D model of the aorta.

In cases where the endoprosthesis is already deployed, this makes it possible to model the actual deployment of the endoprosthesis in 3D. In cases where the endoprosthesis is not deployed or not completely deployed, this allows the surgeon to visualize how the deployment of the endoprosthesis will look if he decides to deploy it in its current position.

Figure 7A:
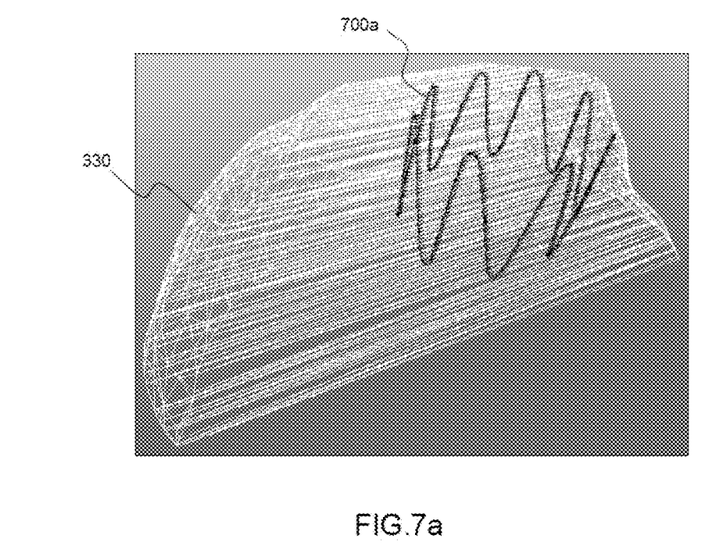
FIG. 7a shows a first example of modelling the deployment of a stent, according to a set of implementations of the invention.
Figure 7B:
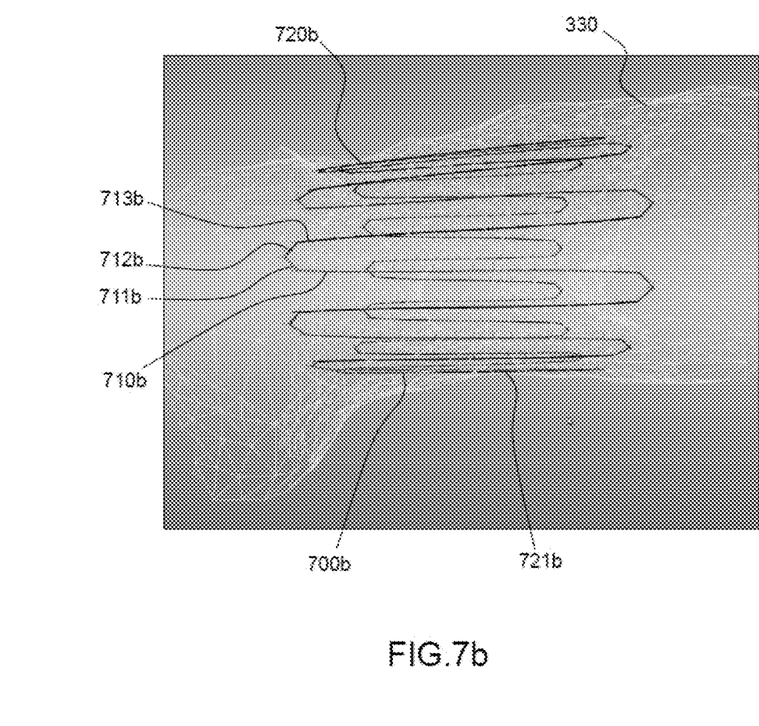
FIG. 7b shows a second example of modelling the deployment of a stent, according to a set of implementations of the invention.

FIGS. 7a and 7b show two examples of modelling of the deployment of a stent according to a set of implementations of the invention.

The model 351 of a stent is formed by a plurality of beam elements modelling the stents. The number of beam elements may be variable depending on the desired complexity.

A model 351 of a stent can be formed, for example, from a hundred or so beam elements.

FIG. 7a shows the initialization of a model 700a (corresponding to an example of the model 351) in the 3D model of the aorta 330. As has been explained above, the steps 330 and 340 make it possible to determine, for each stent, characteristics of a simplified model: position of the characteristic points, rotation about the central axis, etc. These values permit initialization of the position and orientation of the beam elements of the model 351, 700a representing the structure of the stent.

In the example in FIG. 7a, the stent is not yet deployed. In order to simulate the deployment of the stent, it then suffices to simulate the extension of the beam elements from the initialization position to the limits of the 3D model 330 of the aorta.

FIG. 7b shows a stent model deployed in the 3D model of the aorta 330. As has been explained above, the model 700b is formed by a plurality of beam elements, for example the elements 710b, 711b, 712b, 713b. The stent can thus be deployed either to its maximum extension or until the beam elements reach the limits of the aorta, for example at the points 720b, 721b.

The finite element model makes it possible to take into consideration at the same time the constraints within the stent and the interaction between the stent and the aorta.

Since the finite element model representing the structure of the stent is initialized on the basis of the simplified model calculated beforehand, the simple simulation of the deployment of the stent can be effected rapidly, while at the same time very precisely modelling the deployment of the stent.

The method 300 as a whole thus permits a both reliable and rapid calculation of the deployment of an endoprosthesis in the aorta. For example, the method can be carried out in about thirty seconds on standard calculation means, which allows the deployment of the endoprosthesis to be modelled almost in real time.

This result is permitted by the fact that the complete model modelling the structure of each stent (model 351, 700a, 700b), which comprises numerous elements, is initialized by the preceding steps and need only be deployed. Although it is possible to directly model the deployment of a complete model representing the structure of each stent of the endoprosthesis without prior hypothesis, this would take a considerable amount of time incompatible with the performance of an operation in real time.

Returning to FIG. 3, the method 300 comprises a step 360 of displaying the deployed model of the stents. This display can be either in 2D, by superposing the projection of the deployment of the stents on a perioperative 2D image such as the image 200, or in 3D, by displaying the deployment of the stents in 3D and the model of the aorta 330. The display can be shown, for example, on the screens 121 of a medical imaging device.

Provided that the method permits simulation of the deployment of the endoprosthesis in a very precise manner and in real time, the display 360 allows the surgeon real-time visualization of the deployment of the endoprosthesis on the basis of its actual position. This therefore makes it possible to considerably improve the precision of the treatment performed by the surgeon.

In the case where the method is applied to a deployed endoprosthesis, the surgeon can visualize the deployment in 3D. In the case where the method is applied to an endoprosthesis that is not deployed, the surgeon can visualize how the deployment of the endoprosthesis will look, in 3D, if he decides to deploy it on the basis of the current position.

Moreover, this method requires a single image capture in order to simulate the deployment of an endoprosthesis, which avoids the use of multiple injections of contrast agent.

Figure 8:
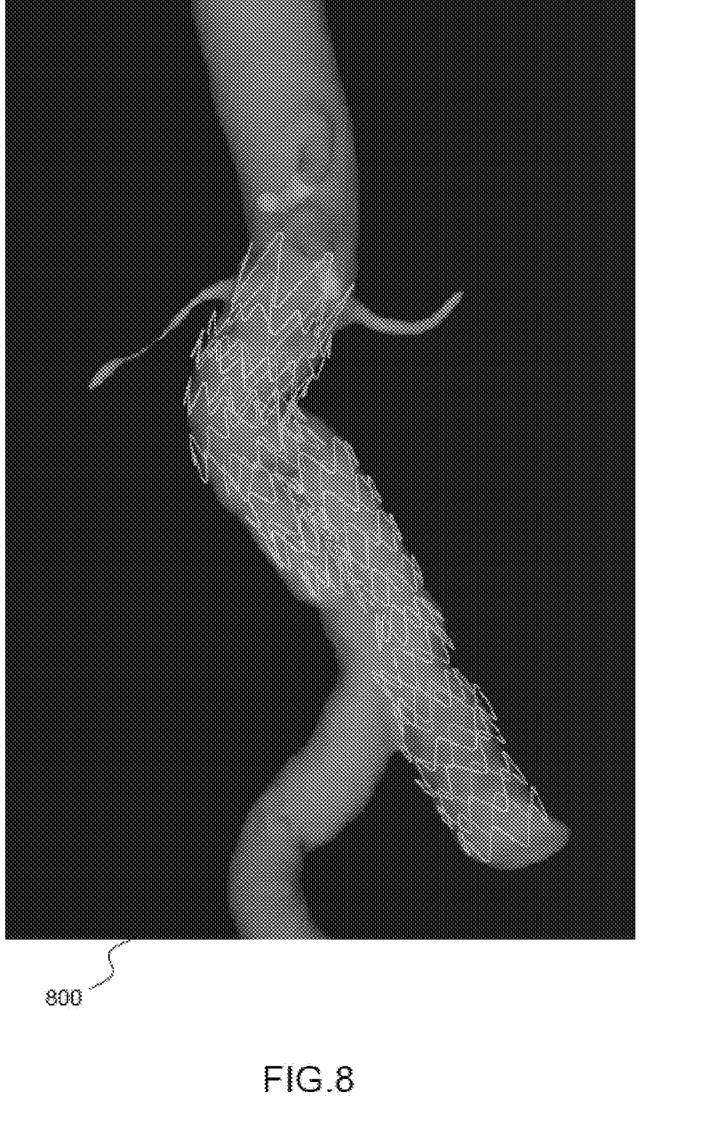
FIG. 8 shows a superposition of the simulation of deployment of a stent on a perioperative image, according to a set of implementations of the invention.

FIG. 8 shows superpositioning of the simulation of deployment of a stent on a perioperative image according to a set of implementations of the invention.

The image 800 shows the superpositioning of the stimulation of the deployment of the endoprosthesis on the 2D imaging obtained from a C-arm. As has been explained above, the invention also permits 3D representation of the simulation of the deployment of the endoprosthesis on the 3D model of the aorta. In the case of 3D visualization, the surgeon can manipulate the representation in order to visualize the prediction of the deployment at different viewing angles.

In both cases, this allows the surgeon to visualize the simulation of the deployment of the endoprosthesis in real time.

The above examples demonstrate the capacity of the invention to permit determination of the deployment of an endoprosthesis. However, they are given solely by way of example and do not in any way limit the scope of the invention as defined in the claims below.

The invention claimed is:

1. A method implemented by an imaging system comprising an imaging device and a calculation device comprising a calculation unit, the imaging device being connected to the calculation device, wherein the method comprises:
   a capture, by the imaging device, of a 2D image of a vascular structure and of an endoprosthesis comprising a plurality of stents, by X-ray;
   an acquisition, by the calculation unit, of a 3D model of the vascular structure;
   an acquisition, by the calculation unit, of a model of an endoprosthesis in the vascular structure;
   a determination, by the calculation unit, from the 2D image, and for each stent, of values comprising at least one position, an angle of intrinsic rotation ($r_{x'}$), and at least one deployment value;
   a simulation, by the calculation unit, of a deployment in the 3D model of the vascular structure, for each stent, of a model of the stent representing a structure of the stent, from the values determined in the determination step, said model of the stent being initialized on a basis of the model of the endoprosthesis; and
   a display, by the calculation device, of the stent models deployed in the simulation step, on one or more display screens; and
   said method being wherein the determination, by the calculation unit, for at least one stent, of its angle of intrinsic rotation ($r_{x'}$) comprises the determination of the angle of intrinsic rotation ($r_{x'}$) for which at least one 3D position projection of at least one radiopaque marker on the stent most closely matches to at least one image of the at least one marker on the 2D image.

2. The method according to claim 1, wherein:
   the 2D image defines a 3D reference frame ($R_{im}$) comprising a vertical axis (x) and a horizontal axis (y) and a depth axis (z) of the image;
   in the endoprosthesis model, each stent is defined by:
      at least one position of at least one characteristic point (P0, P1, P2) and an orientation, which are defined by at least 6 degrees of freedom, including:
         the 3D position of a first characteristic point (P0) of the stent in the reference frame;
         the angle of intrinsic rotation ($r_{x'}$);
         the at least one deployment value of the stent, defined about its central axis;
      the model of the stent is formed by a plurality of interconnected beam elements;
   said method comprising:
      determination, by the calculation unit, from the 2D image, and for each stent, of at least one position, at least one orientation, and at least one deployment value; of the at least one characteristic point along the vertical axis (x) and horizontal axis (y) and the at least one deployment value of said stent; and
      determination, by the calculation unit, for at least one stent, of its angle of intrinsic rotation ($r_{x'}$).

3. The method according to claim 1, wherein the position and orientation of each stent are defined by 3D positions of three characteristic points (P0, P1, P2) corresponding respectively to a center, an upper end and a lower end of the stent along its central axis (x'), and the angle of intrinsic rotation of the stent about its central axis (x').

4. The method according to claim 1, wherein the angle of intrinsic rotation ($r_{x'}$) is obtained by an execution of a loop minimizing a distance between the at least one projection and the at least one image of the at least one marker on the 2D image, as a function of the angle of intrinsic rotation ($r_{x'}$).

5. The method according to claim 1, wherein the determination, by the calculation unit, for at least one stent, of its angle of intrinsic rotation ($r_{x'}$) comprises modelling the stent in a form of a beam element of a finite element model, between a characteristic point representing an upper end of a central axis of the stent (P1) and a characteristic point representing a lower end of the central axis of the stent (P2), wherein the characteristic points are free of displacements along a depth axis (z).

6. The method according to claim 5, wherein:
   the endoprosthesis is represented in the form of a finite element model wherein:
      each stent is modelled by a beam element, successive stents being connected to each other by at least one beam element;
      positions of the characteristic points of the stents whose maximum diameter of deployment is greater than or equal to the diameter of the vascular structure at the deployment position are fixed along a vertical axis (x), a horizontal axis (y) and a depth axis (z);
      the positions of the characteristic points of the stents whose maximum diameter of deployment is less than the diameter of the vascular structure at the deployment position are fixed along the vertical axis (x) and horizontal axis (y) and are free in displacement along the depth axis (z); and
   the positions of the characteristic points of the stents whose maximum diameter of deployment is less than the diameter of the vascular structure at the deployment position along the depth axis (z) are determined by a mechanical equilibrium of the finite element model.

7. The method according to claim 1, wherein the display of deployed stent models comprises a superposed display of a projection of the stent models on the 2D image of the vascular structure.

8. The method according to claim 1, wherein the display of deployed stent models comprises the 3D display of the deployed stent models and of the 3D model of the vascular structure.

9. The method according to claim 1, wherein the 3D model of the vascular structure is a finite element model representing a central line of the vascular structure by beam elements.

10. A computer program product comprising computer code elements configured to execute a method according to claim 1 when said program is executed on a calculation unit of a calculation device.

11. An imaging system comprising an imaging device and a calculation device, the imaging device being connected to the calculation device, wherein:
- the imaging device is configured to capture a 2D image of a vascular structure and of an endoprosthesis comprising a plurality of stents, by X-ray;
- the calculation device comprises:
    - at least one input port configured to receive a 2D image of the vascular structure captured by X-ray:
    - at least one calculation unit configured to:
        - acquire a 3D model of the vascular structure;
        - acquire a model of an endoprosthesis in the vascular structure;
        - determine, from the 2D image, and for each stent, values comprising at least one position, an angle of intrinsic rotation ($r_{x'}$), and at least one deployment value; and
        - simulate the deployment in the 3D model of the vascular structure, for each stent, of a model of the stent representing the structure of the stent, from the values determined in the determination step, said model of the stent being initialized on the basis of the model of the endoprosthesis;
- the calculation device being configured to display the stent models deployed in the simulation step, on one or more screens; and
    - wherein the determination, by the calculation unit, for at least one stent, of its angle of intrinsic rotation ($r_{x'}$) comprises the determination of the angle of intrinsic rotation ($r_{x'}$) for which at least one 3D position projection of at least one radiopaque marker on the stent most closely matches to at least one image of the at least one marker on the 2D image.

* * * * *